United States Patent
Melikechi et al.

(10) Patent No.: US 7,407,616 B2
(45) Date of Patent: *Aug. 5, 2008

(54) METHOD FOR PHOTO-CURING POLYMERIZABLE COMPOSITIONS WITH PULSED LIGHT

(75) Inventors: Noureddine Melikechi, Dover, DE (US); Ranjit S. Pandher, Plainsboro, NJ (US)

(73) Assignee: New Photonics, LLC, Dover, DE (US)

( * ) Notice: Subject to any disclaimer, the term of this patent is extended or adjusted under 35 U.S.C. 154(b) by 337 days.

This patent is subject to a terminal disclaimer.

(21) Appl. No.: 11/056,588

(22) Filed: Feb. 11, 2005

(65) Prior Publication Data

US 2006/0183811 A1 Aug. 17, 2006

(51) Int. Cl.
*A61C 5/00* (2006.01)
*B29C 35/08* (2006.01)

(52) U.S. Cl. .............. 264/494; 264/496; 522/1; 522/48; 522/182; 523/116; 523/117; 433/226

(58) Field of Classification Search ........... 264/494, 264/496; 522/1, 48, 182; 523/116, 117; 433/226

See application file for complete search history.

(56) References Cited

U.S. PATENT DOCUMENTS

| | | | |
|---|---|---|---|
| 4,112,335 A | 9/1978 | Gonser | 315/241 R |
| 4,229,658 A | 10/1980 | Gonser | 250/504 H |
| 4,309,617 A | 1/1982 | Long | 250/504 H |
| 4,358,344 A | 11/1982 | Sass et al. | 201/4 |
| 4,411,625 A | 10/1983 | Koblitz et al. | 433/217 |
| 4,437,836 A | 3/1984 | Schmitz-Josten et al. | 433/199 |
| 4,553,940 A | 11/1985 | Koblitz et al. | 523/115 |
| 4,957,441 A * | 9/1990 | Bryan | 433/228.1 |
| 5,147,204 A | 9/1992 | Patten et al. | 433/229 |
| 5,420,768 A | 5/1995 | Kennedy | 362/119 |
| 5,616,141 A | 4/1997 | Cipolla | 606/15 |
| 5,634,711 A | 6/1997 | Kennedy et al. | 362/119 |
| 5,711,665 A | 1/1998 | Adam et al. | 433/9 |
| 5,879,159 A | 3/1999 | Cipolla | 433/29 |
| 5,885,082 A | 3/1999 | Levy | 433/215 |
| 6,001,297 A * | 12/1999 | Partanen et al. | 264/401 |
| 6,008,264 A * | 12/1999 | Ostler et al. | 522/4 |
| 6,077,073 A | 6/2000 | Jacob | 433/29 |

(Continued)

FOREIGN PATENT DOCUMENTS

EP 1 336 389 A1 * 8/2003

(Continued)

OTHER PUBLICATIONS

"Possible improvements of clinical properties of dental composite materials with pulsed blue laser curing" by Zrinka Tarle, Andrej Meniga, Mira Ristic, Jozo Sutalo and Goran Pichler, Croatia Chemica Acta 71, 777-787 (1998).

(Continued)

*Primary Examiner*—Susan W Berman
(74) *Attorney, Agent, or Firm*—Michael W. Ferrell

(57) ABSTRACT

A method for curing polymerizable compositions by irradiating the compositions with a pulsed light that is emitted from an LED. The method of the present invention is especially suitable for curing dental compositions.

18 Claims, 5 Drawing Sheets

U.S. PATENT DOCUMENTS

| | | | |
|---|---|---|---|
| 6,099,520 A | 8/2000 | Shimoji | 606/2 |
| 6,102,696 A | 8/2000 | Osterwalder et al. | 433/29 |
| 6,103,203 A | 8/2000 | Fischer | 422/186 |
| 6,139,175 A | 10/2000 | Tomioka et al. | 362/574 |
| 6,159,005 A | 12/2000 | Herold et al. | 433/29 |
| 6,171,105 B1 | 1/2001 | Sarmadi | 433/29 |
| 6,200,134 B1 | 3/2001 | Kovac et al. | 433/29 |
| 6,233,039 B1 | 5/2001 | Yen et al. | |
| 6,282,013 B1 * | 8/2001 | Ostler et al. | 359/309 |
| 6,318,996 B1 | 11/2001 | Melikechi et al. | 433/29 |
| 6,384,099 B1 * | 5/2002 | Ostler et al. | 522/4 |
| 6,387,980 B2 | 5/2002 | Lu et al. | 523/116 |
| 6,468,077 B1 | 10/2002 | Melikechi et al. | 433/29 |
| 6,482,004 B1 | 11/2002 | Senn et al. | 433/29 |
| 6,511,317 B2 | 1/2003 | Melikechi et al. | 433/29 |
| 6,602,074 B1 | 8/2003 | Suh et al. | 433/228.1 |
| 6,638,063 B2 | 10/2003 | Otsuka | 433/92 |
| 6,755,647 B2 | 6/2004 | Melikechi et al. | 433/29 |
| 7,134,875 B2 * | 11/2006 | Oxman et al. | 433/226 |
| 2001/0017776 A1 | 8/2001 | Otsuka | 433/29 |

FOREIGN PATENT DOCUMENTS

| | | |
|---|---|---|
| WO | WO 99/35995 | 7/1999 |

OTHER PUBLICATIONS

"Calibration of FTIR conversion analysis of contemporary dental resin Composites." by Rueggeberg, et al., Dent Mater, 1990 6:241-249.

"Pulsed Blue Laser Curing of Hybrid Composites Resins", Meniga et al. Biomaterials 18, 1349-1354, 1997.

"Dentistry Polymer-Based Filling, Restorative and Luting Materials" ISO 4049, 1998.

* cited by examiner

METHOD FOR PHOTO-CURING POLYMERIZABLE COMPOSITIONS WITH PULSED LIGHT

TECHNICAL FIELD

The present invention relates generally to a method of photo-curing polymerizable compositions and more particularly to curing polymerizable compositions with pulsed light which is emitted from an LED.

BACKGROUND

Polymerizable compositions materials may cure, or harden, when they are subjected to light because a polymerization reaction is photo-initiated. Although these type of compositions have a wide range of applications, they are especially useful in the field of dentistry for adhesion, sealing and restoration. These are known as "photo-curable dental compositions" (see for example, those dental compositions described in U.S. Pat. Nos. 4,553,940, 4,437,836, 4,411,625 and 6,387,980, the entireties of which are incorporated herein by reference).

The quality of the cured compositions is important in all photo-curable polymer applications, e.g., semiconductor applications, but is of special concern in the field of dentistry. Characteristics which are significant in evaluating the quality of a photo-cured polymer include hardness, depth of cure, polymerization yield, and uniformity.

Photo-curable dental compositions generally harden when exposed to radiation having wavelengths in the visible range. Photo-cured dental compositions are convenient for use by a dentist because the curing process can be initiated when the dental composition has been accurately placed in its proper position. A source of radiation energy positioned proximate to the material to be hardened, for example an appropriate amount of composition placed inside a tooth cavity, is activated to initiate polymerization and subsequent curing of the composition to secure the repair. Early methods for curing photosensitive dental compositions included dental guns and other apparatuses for producing concentrated beams of UV radiation. See U.S. Pat. Nos. 4,112,335 and 4,229,658, for example. Later, visible light curable dental compositions were used and dental radiation guns for producing concentrated visible light were provided like that disclosed in U.S. Pat. Nos. 4,385,344 and 6,171,105.

U.S. Pat. No. 4,309,617 to Long discloses an apparatus for providing controlled flashes of radiation, including a handpiece within which is mounted a gaseous discharge tube and a light pipe for conducting the radiation, enabling it to be directed into an oral cavity to effect in situ curing of radiation polymerizable resins used as dental restoratives. The flash durations, which can be 0.5 milliseconds in duration (See Col. 6 lines 32-34) and intervals are controlled to minimize generation of heat.

There is shown in U.S. Pat. No. 5,420,768 to Kennedy, for instance, a portable photo-curing device that has a light emitting diode matrix energized with battery power. The '768 patent notes in Col. 2 that light emitting diodes (LEDs) of various selected colors may be formed on the module by using selected color dyes so that the emitted light is a pure white light or a combination of selected color lights to provide a predetermined photo curing effect. The light emitted by the LEDs may have a peak wavelength of 470 nm which is used for photo curing purposes.

U.S. Pat. No. 5,634,711 to Kennedy et al. discloses a portable light emitting device suitable for medical and industrial photo curing. Typically, the LEDs are driven by a pulsed power supply in order to minimize heat generation. It is noted in the '711 patent that various applications require different light dosage values. For example, it is noted in Col. 1, lines 39 and following that light dosage values in the range of up to 400 mW/cm$^2$ are typically required for dental applications. On the other hand, a medical application such as photodynamic therapy of psoriasis and basal cells requires much lower power typically in the range of up to 100 mW/cm$^2$. The device according to the '711 patent includes generally a power supply, a housing, and a substrate upon which a plurality of light emitting diodes are mounted. It can be seen from FIGS. 1 and 6 of the '711 patent that the LED array is generally planar and that the device typically includes an optical assembly such as a fiber optic taper. Here again, the LED can comprise "blue" LEDs with a spectral emission in the 470 nanometer range.

U.S. Pat. No. 5,885,082 to Levy discloses the use of laser radiation having a selected wavelength and being in the form of pulses for cutting bone and performing dental procedures. There is disclosed in Column 4, lines 27 and following a filling material for teeth constituted by a mixture formed from a liquid component composed of phosphoric acid and water and a powder component composed of a ceramic and hydroxyapatite, with the ingredients mixed in a proportion to form a paste having a consistency such that the paste is workable and sufficiently self supporting to be applied to the opening with a spatula and remain in place. The '082 patent does not involve a photocuring process and the material is not a dental polymer composite. The high peak power of the laser is believed to be used only for cutting and possibly hardening of the cement due to heat.

U.S. Pat. No. 6,159,005 to Harold et al. discloses an apparatus for photopolymerizing synthetic materials, specifically dental materials containing camphorquinone or phosphine oxide as photoinitiators and includes a light source constituted by a semiconductor base solid state radiation emitter which emits in the blue spectral range. Since the radiation emitter emits in a relatively limited spectral range, excess heat radiation is avoided. The overall device is formed as a relatively small lightweight device with a built in battery. The device further includes a light-conducting rod in order to direct radiation to the desired location. According to the '005, patent an essential photoinitiator in dental materials is typically camphorquinone or phosphine oxide which absorbs a broad band within the blue spectral range, with an absorption maximum of about 472 nm and 430 nm, respectively. The patent further notes that depending on the color of the material, the polymerization reaction requires light having an intensity of at least 1 to 5 mW/cm$^2$ within a very thin layer. In the practice of polymerizing tooth fillings or dental replacement parts, a light intensity of at least 250 mW/cm$^2$ is required within an appropriate period of time to achieve polymerization of sufficient degree and depth. Commercially available dental polymerization apparatuses, at least according to this '005 patent, emit light at an intensity of about 400-500 mW/cm$^2$ sometimes up to 700 mW/cm$^2$. The solid state radiation emitter according to the '005 patent is preferably a laser diode which emits a forward beam used for the polymerization proper and a backward beam used as a reference beam for controlling the intensity of the polymerization beam.

U.S. Pat. No. 6,482,004 to Senn et al. discloses a light curing device and method for curing light-polymerizable dental materials. Such light curing device includes a control circuit which controls the light output of the light source according to a predetermined output profile. The output profile includes an initial curing time wherein the output is increased over a period of time and a main curing time wherein the output is alternated at an alternating high and low output value. Further the output values are subject to change between the initial curing time and the main curing time.

Still further devices and techniques have been proposed as noted below. "*Possible improvements of clinical properties of dental composite materials with pulsed blue laser curing*" by Zrinka Tarle, Andrej Meniga, Mira Ristic, Jozo Sutalo and Goran Pichler, Croatia Chemica Acta 71, 777-787 (1998) compare the degree of conversion and polymerization shrinkage of hybrid and microfilled composite materials (see Table 1 of paper) cured using a pulsed blue laser system and a "standard" curing unit operating in a continuous wave (cw) mode (Heliolux GTE curing unit of 500 mW/cm$^2$). The goal of the work was to determine whether optimal degree of conversion and minimal polymerization shrinkage of the composite restorative resin could be achieved using nanosecond lasers operating at 468 nm. This wavelength closely matches the maximum of the camphorquinine absorption spectrum. The authors used an excimer pumped dye laser to generate the desired pulsed optical energy necessary for the .photopolymerization. As such, the optical pulses generated although tunable in wavelength, have a fixed temporal characteristics (20 nanosecond laser pulses at a repetition rate of 10 Hz) set by the nature of the lasers used.

"Pulsed blue laser curing of hybrid composite resins" by Andrej Meniga, Zrinka Tarle, Mira Ristic, Jozo Sutalo and Goran Pichler, Biomaterials 18, 1349-1354 (1997) reports on the effect of photopolymerization of light and dark shades cured using 10 mJ of 20 nanosesond laser pulsed dye lasers operating at 468 nm.

U.S. Pat. No. 6,102,696 to Osterwalder et al. discloses a self-contained light source for curing light initiated resins used to coat teeth as veneers and fill cavities and chips in teeth in aesthetic or restorative procedures. The source includes an elongated container holding a battery and an electronic compartment in one end and a light emitting window at the other. A plurality of closely spaced light emitters, typically light emitting diodes or laser diodes are arrayed in a radial or arcuate configuration to direct light to a common focal point. The light is directed out of the container toward a tooth bearing the resin to be cured to a hard stable state. The light emitters are chosen so that they generate light to which the resin curing initiator is sensitive. The wavelength range of the emitted light falls typically within the blue part of the spectrum. It can be seen from FIG. 2 and 3 of the '696 patent that LEDs are typically arrayed in an arcuate configuration about a focal point 38. The apparatus is reported to be useful for curing dental resins including a 1:1 mixture by weight of bis-phenol-2bis (2-hydroxypropyl) methacrylate and tri (ethylene glycol) dimethacrylate monomers. The resinous mixture may further include a camphorquinone photoinitiator and a tertiary amine reducing agent. Fillers such as silica particles and colorants are typically included to achieve the desired hardness level and color.

U.S. Pat. No. 6,602,074 to Suh et al. discloses a process for preparing dental restorations which includes the application of light to a composite of intensity sufficient to penetrate the composite to initiate polymerization. Light application is suspended for a period of time sufficient to allow for the relaxation of internal stresses created by the initial polymerization of the composite. (Claim 1 requires suspension of the light for a period of 10 seconds.) Light is subsequently applied to the composite to complete polymerization.

WIPO Publication No. WO 99/35995 (essentially the same as U.S. Pat. No. 6,200,134) to Kovac et al. discloses a curing device for curing light sensitive compounds. The device includes generally a housing and an array of solid state light emitting diodes for having wavelengths in the range of 400-500 nm. Preferably, a peak wavelength of 470 nm is generated. The device further comprises an optical fiber light pipe for capturing the light and transmitting a beam of the light to the dental or other work surface containing a light curable compound. An optical lens may be used for focusing the light into the light pipe. It is noted on page 8 of this publication that 200-500 LEDs are used for creating the necessary light power needed for curing available dental compounds. In one embodiment of the device described, 96 LEDs are used whereas in a prototype e.g., an embodiment was made wherein 9 LEDs were utilized. See page 14. It is further noted in the publication that LEDs which include integral lenses may be employed. The discussion on page 20 and following notes that state that radiated power levels of approximately 200 mW/cm$^2$ or greater are generally necessary for curing the available dental compounds. Other intensities may be necessary for curing other light sensitive compounds.

There is a need for methods of curing polymerizable compositions where the cured composition is of a higher quality. There is also a need to reduce the time necessary to cure polymerizable compositions. The applicants in the present invention have surprisingly found that, contrary to standard practices, the use of optical radiation with specific pulse duration and repetition rate yields better quality of cure than using comparable continuous wave optical radiation.

SUMMARY OF THE INVENTION

Very generally, there is provided in accordance with the present invention a method for curing polymerizable compositions using pulsed light. The method comprises irradiating the polymerizable compositions with pulsed light which is emitted from at least one LED, where the light has a pulse duration of between about 0.05 to about 75 μs and a pulse repetition time of about 0.25 to about 100 μs.

The compositions which are pulse-cured according to the present invention typically have higher hardness values than like compositions which are cured for the same total exposure with a continuous wave light source having the same emission spectrum. The cured compositions have a preferred hardness value of 40, and more preferably 50, on the Barber-Coleman Hardness Scale when the composition is cured for 20 seconds at a power level of 20 mW. Also, the method of the present invention usually requires less total exposure to cure a composition to a certain depth of cure than is required for a continuous wave light source with a similar emission spectrum.

In some embodiments the polymerizable compositions used in the inventive method are photo-curable dental compositions and may include liquid acrylic monomers. It is further contemplated that the polymerizable compositions may contain camphorquinone as a photoinitiator.

The method of the present invention may suitably be used with an LED which has an excitation peak that falls within 40 nm of the absorption peak of a photoinitiator in the composition. Preferably the LED emits blue light and even more preferably emits light having an excitation peak falling between 440 and 500 nm on the electromagnetic spectrum.

The pulse duration used in the method of the present invention is typically between about 0.1 to about 10 μs, and more desirably should be between about 2 to about 3 μs. The pulse period is usually between about 1 to about 10 μs, and should preferably be from about 2 to about 5 μs. Typically, the pulse duration and the pulse period are selected so that the pulse operates with a duty cycle of from about 5 to about 50%.

The compositions cured according to the present invention generally have cure depths of at least about 2.8 mm, and should preferably have cure depths of at least about 3 mm.

Further features of the invention will become apparent from the discussion which follows.

BRIEF DESCRIPTION OF THE FIGURES

The invention is described in detail below in connection with the appended drawings wherein like numerals designate like parts and wherein.

DETAILED DESCRIPTION

Figure 1:
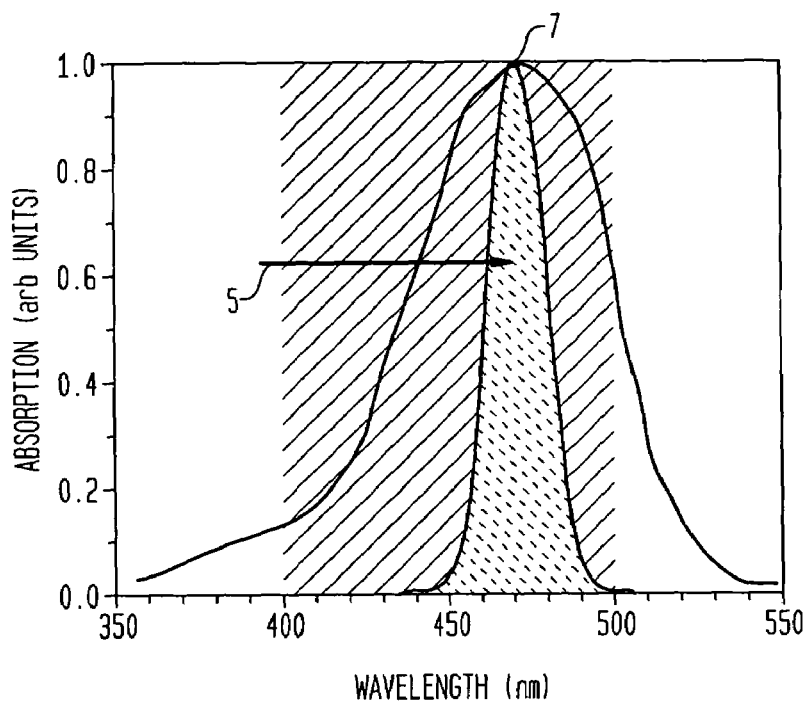
FIG. 1 shows the absorption spectrum of camphorquinone and the emission spectral characteristics for a blue LED light source, showing an excitation peak at about 470 nm.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined, terminology is given its ordinary meaning.

"Pulse duration," also called "pulse width" refers to the time interval that separates two adjacent points with amplitudes equal to half the peak amplitude. The pulse duration is given in time units, usually in µs.

"Pulse repetition rate" is the number of pulses per unit time. It usually has frequency units such as Hertz (Hz).

"Pulse period," also called "pulse repetition interval" is the reciprocal of pulse repetition rate. The pulse period is given in time units, preferably µs.

"Duty cycle" is the ratio of pulse duration to pulse period and is a dimensionless parameter, but may be expressed as a percentage.

"Total exposure," "exposure," "total energy," and like terminology refers to the amount of energy that is emitted by a light source in proximity with a polymerizable composition to cure the composition over a cure duration. For a continuous wave source it may be obtained from multiplying the power of the light by the duration of the cure. For pulsed light, it may be determined by multiplying the power of the light, the duration of the cure, the pulse repetition rate, and the pulse duration. Total exposure is reported in energy units, preferably millijoules (mJ).

"Polymerizable compositions," "photo-curable compositions," and like terminology refers to any composition which may be cured by undergoing polymerization when exposed to light. Photocurable resins are very common, especially in the field of dentistry. Other uses of polymerizable compositions include photo-curable epoxy resins for use in electronics, optoelectronics, and space craft applications; medical and biomaterial applications; and coatings, adhesives, and printing inks. Polymerizable dental compositions typically comprise liquid acrylic monomers, particulate fillers such as glass or ceramic particles, and photo-initiators such as camphorquinone. Exemplary polymerizable compositions for use in the present invention may include: TPH Spectrum composite (shade A3.5) from Dentsply International, Inc. wherein the resin matrix of the composite consists of a BisGMA-adduct (adduct of 2,2-Bis[4-2-hydroxy-3-methacryloyloxpropoxy)-phenyl]propane with hexamethylene diisocyanate), ethoxylated Bisphenol-A-dimethacrylate (Bis-EMA, 2,2-Bis[4-(2-methacryloyloxyethoxy)-phenyl]propane) and triethylene glycol dimethacrylate. The combination of barium alumino boro silicate glass filler and colloidal silica results in a hybrid composite with good strength and wear resistance for posterior use, combined with high surface luster and smoothness, which is an essential property for anterior use of a composite; as well as adhesives including light cure resin bond from Reliance which includes Bis-GMA and ethoxylated derivative, polyethylene glycol dimethacrylate amine, ketone photoinitiator. Filler particles include 60-99% fused silica and some amorphous silica. Other acceptable compositions for use in the present invention will be apparent to those skilled in the art.

LEDs are semiconductor diodes that emit light when conducting a current. The semiconducting material is doped in a common manner to create a pn junction. When an electron passes through the semiconductor material, it falls to a lower energy lever, emitting light. One or many LEDs may be used with the present invention, and, if in an array, they may be arranged in any pattern. For the present invention it is preferred that the light source operates at a wavelength in the range of 400-500 nm. It is also desirable that light source has an excitation peak that is within about 40 nm of the peak absorption of a photoinitiator that is in the polymerizable composition. FIG. 1 shows the absorption spectrum of camphoquinone. FIG. 1 illustrates that Blue LEDs are preferable when camphoquinone is used as a photo initiator because they have an excitation peak 5 that coincides closely with the absorption peak of camphoquinone 7 at about 470 nm. Exemplary LEDs useful in practicing the present invention include the Cree XB-900 series from Cree of Durham, which are rated for 65-100 mW of optical output power at typical operating current of 350 mA in cw mode operation. In the examples below which use Cree LEDs, three Cree LEDs were assembled together to obtain high peak optical power. In addition, the LEDs were mounted at three different heights so that the intensity at the curing site would be less sensitive to operating distance. Other suitable LEDs include a system available from Lamina Ceramics which employs 42 LEDs mounted on ceramic substrates for a heat sink, and which emits light in a cone of 150-160 degrees (also used in some examples, below).

Figure 2:
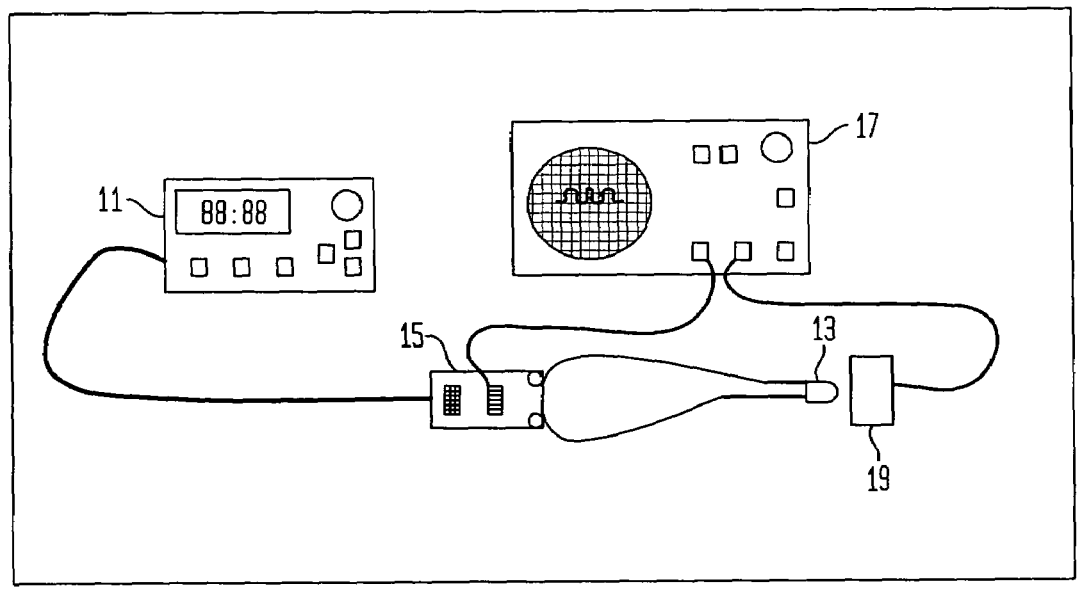
FIG. 2 is a schematic diagram of the instrumentation and set up used to generate pulsed light from LEDs.

Any acceptable method of pulsing the light at the required intensity, pulse duration, and pulse repetition rate may be used. Useful devices include those that generate a power output of from about 20 mW to about 800 mW. Pulse durations should be from about 0.05 to about 75 µs and pulse periods should be from about 0.25 to about 100 µs. However, it is preferred that the pulse duration be from about 0.1 to about 10 µs and that the pulse period be from about 1 to about 10 µs. Even more preferred, the pulse duration should be from about 2 to 3 µs and the pulse periods be about 2 to about 5 µs. Typically the pulses operate with a duty cycle of between about 5 to about 50%. FIG. 2 illustrates the set up used in the examples below which employ pulsed light. A Diode Laser Current Pulse generator ("LDP") 11 which is capable of delivering a maximum current of 3 A (model LDP3840, available from ILX lightwave) was used to drive the LEDs 13. A connector card 15 was also used between the LDP and the LED systems for impedance matching purposes. A potentiometer, soldered to the card, allows phase match of the LED system impedance to that of the LDP. It is also desirable to use a 270 Ω resistor in parallel to the LED system. When attempting to determine ideal pulse durations and repetition rates, the LDP should be operated in external trigger mode with a fixed pulse width. A TTL pulse from a signal generator with variable frequency can provide the external trigger. For measurement purposes, a digital oscilloscope 17 may be connected to a photodiode 19 and the connector card.

Continuous wave light sources, sometimes referred to as cw are widely available, especially in the field of dentistry. In the examples below which use a cw light, an L. E. Demetron (Kerr) device was used which employs an array of four LEDs.

In order to demonstrate the improved results of the inventive process, samples which were irradiated using pulsed light are compared with samples 30 which were irradiated with continuous wave light. All samples cured using pulsed light were subjected to square pulses. The polymerizable composition used in the following examples is Dentsply TPH Spetrum Shade A 3.5. The samples were prepared by slightly over-filling them into a stainless steel mold with a diameter of 4 mm and a thickness of 7 mm. The mold was then pressed between two glass plates to firmly pack the composite in the mold. The mold was irradiated with either continuous wave light or pulsed light at various times, intensities, exposures, pulse durations, pulse periods, etc. The resulting compositions were tested for depth of cure and/or hardness values using the following methods. The test method used to determine depth of cure was done in accordance with ISO 4049: 1998 entitled "*Dentistry-polymer-based filling, restorative and luting materials.*" Hardness was measured using a Barber-Coleman impressor (model GYGJ-934-1). The impressor was calibrated using two standard aluminum discs that cover the range needed for these examples. The hardness values are reported according to the Barber-Coleman hardness scale.

EXAMPLE 1

Figure 3:
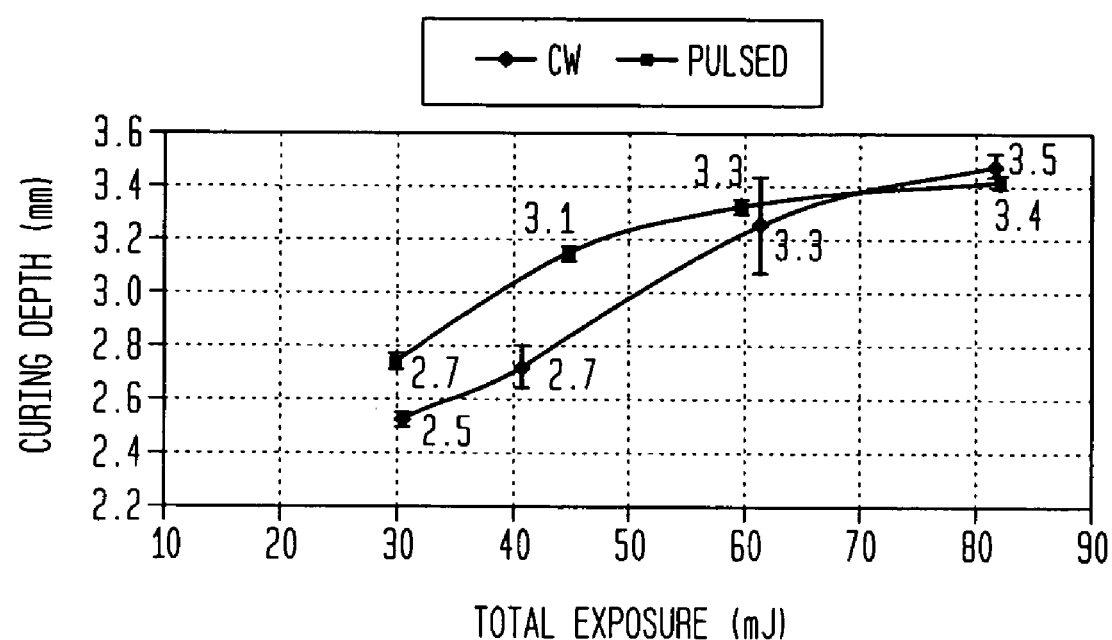
FIG. 3 shows the relationship between depth of cure and total exposure using a cw light and a pulsed light having a 10 µs pulse duration at a 10% duty cycle.
Figure 4:
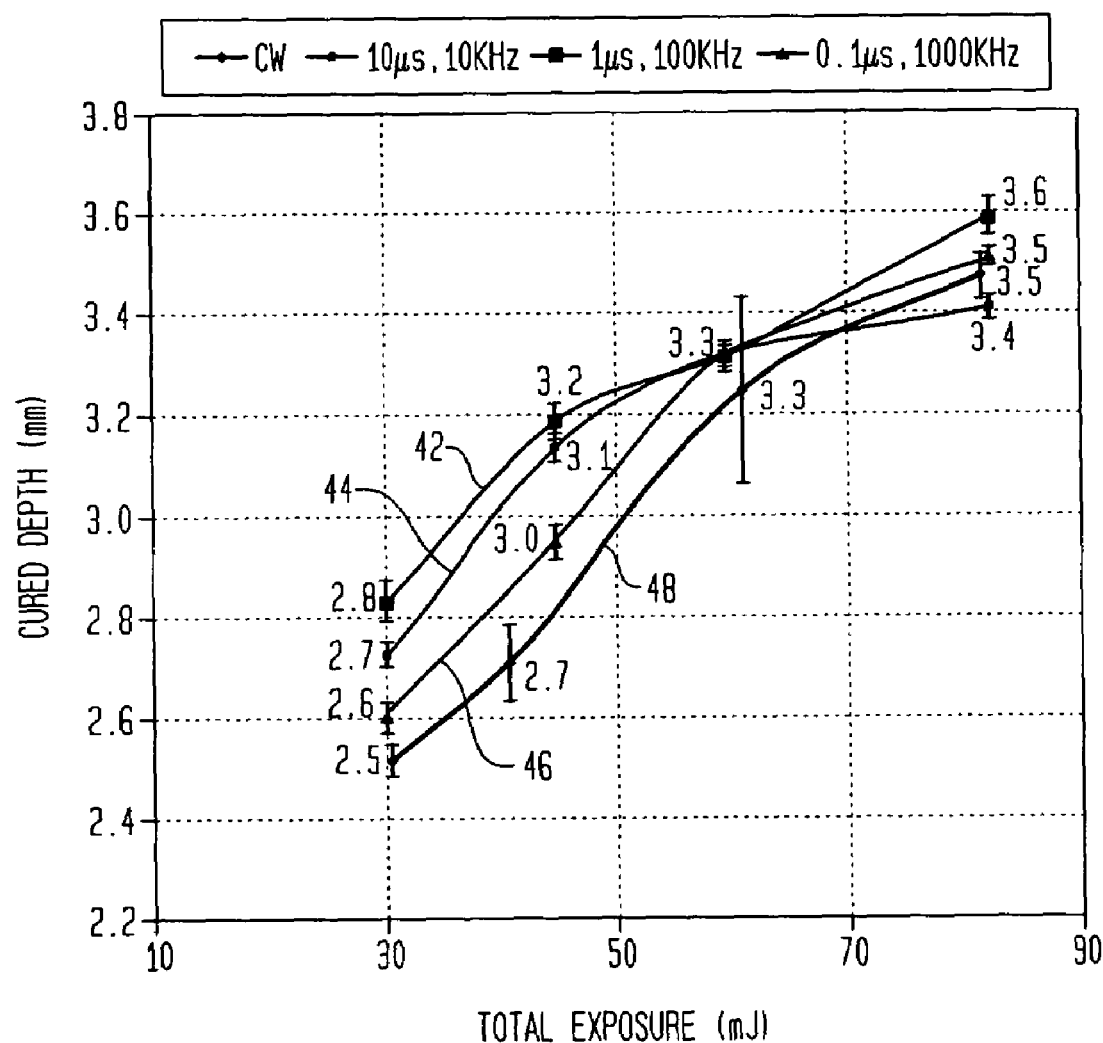
FIG. 4 shows a comparison of cure depths of samples cured with cw and pulsed light with varying pulse durations operating at 10% duty cycle.

Samples of photo-curable materials were irradiated with pulsed light having various pulse widths and frequencies over a range of exposures. The depth of cure measured for samples cured with pulsed light was compared to the depth of cure measured for samples cured with continuous wave light over the same range of exposures. At a given exposure, samples cured with pulsed light had a greater depth of cure than samples cured with conventional continuous wave light. Without intending to be bound by theory, it is believed that a photo-polymerization process is triggered with each pulse of light and that the polymerization reaction auto-completes during the repetition interval. FIG. 3 illustrates the results of a sample cured with pulsed light having a 10 μs pulse duration at a 10% duty cycle and a sample cured with continuous wave light. As shown in FIG. 3, samples of compositions which were cured with pulsed light showed a better depth profile for most exposure values when compared with the samples cured with a continuous wave light. FIG. 4 shows the results for three samples that were irradiated with pulsed light at various pulse durations and pulse repetition rates at a 10% duty cycle, as well as a continuous wave sample. Line 42 shows the cure depth profile for samples cured with light having a pulse width of 1 μs over an exposure range of from about 30 to about 85 mJ. Line 44 shows the cure depth profile for samples cured with light having a pulse duration of 10 μs over an exposure range of from about 30 to about 85 mJ. Line 46 shows the cure depth profile for samples cured with light having a pulse duration of 0.1 μs over an exposure range of from about 30 to about 85 mJ. Line 48 shows the sample cured with a continuous wave source. The cure depths affected for the samples cured with pulsed light were as much as 15% greater at a given exposure than the cure depth resulting from exposure to continuous wave light 48. Alternatively analyzed, a given cure depth can be achieved more efficiently (at a lower total exposure), or faster, with pulsed light as seen by profiles 42, 44 and 46. FIG. 4 also shows that the sample which was pulsed with a pulse duration of 1 μs exhibited the most efficient cure of those tested.

EXAMPLE 2

Figure 5:
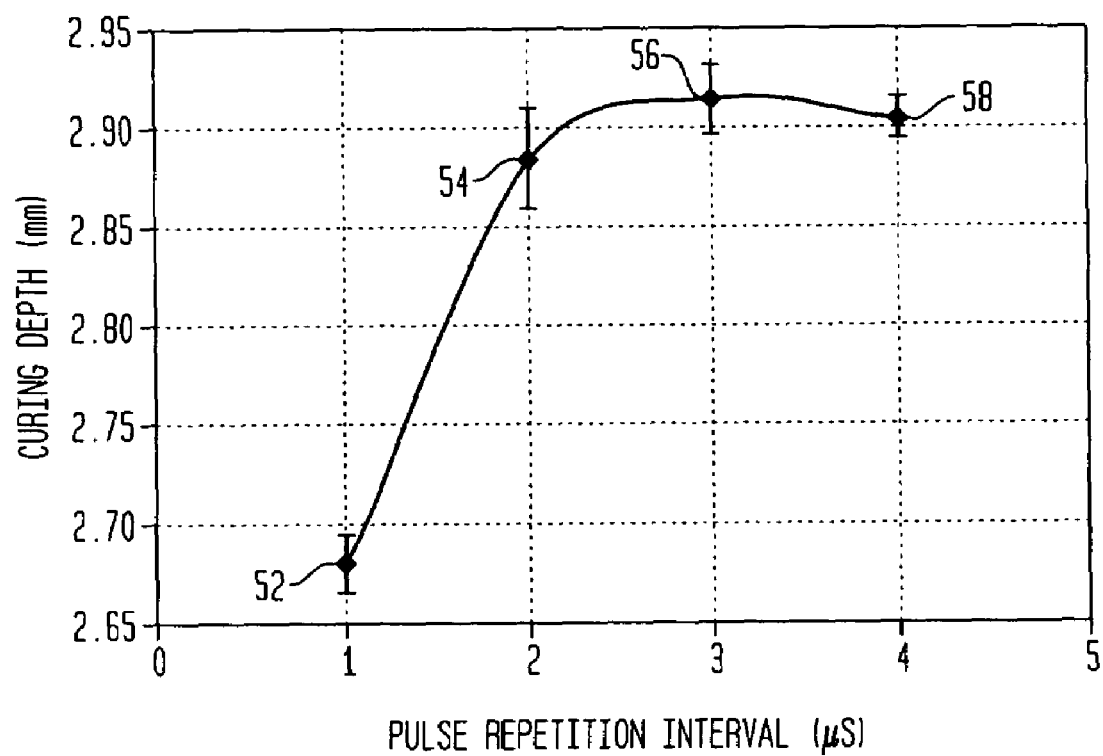
FIG. 5 shows the curing depth dependence on the pulse repetition interval for a constant exposure. The pulse width is 0.1 µs for all measurements.

Samples were irradiated with a pulse duration of 0.1 μs with varying pulse repetition intervals and then the depth of cure was tested. As can be seen in FIG. 5, an increase in the pulse repetition interval results in an increase in depth of cure for samples irradiated with pulsed light. More specifically, a sample irradiated with a pulsed light having a pulse repetition interval of 1 μs is cured to an average depth of about 2.68 mm 52 whereas a sample irradiated with a pulsed light having a pulse repetition interval of 2 μs is cured to an average depth of about 2.89 mm 54. Cure depths measured for similar samples irradiated with light pulsed at pulse repetition intervals of 3 μs 56 and 4 μs 58 were 2.92 mm and 2.91 mm respectively. Thus, for these samples, the photo-polymerization reaction initiated by the light pulse is nearly completed in about 3 μs.

For samples irradiated with pulsed light, note that as the pulse repetition interval increases (which corresponds to a decrease in the pulse frequency), the depth of cure for that sample increases up to a point beyond which there is no change. Therefore, Applicants have shown that there is an optimum range of the pulse repetition interval (PRI). This range yields the most efficient photo-curing process and results in maximum decrease in total exposure to achieve a required depth of cure.

EXAMPLE 3

Figure 6:
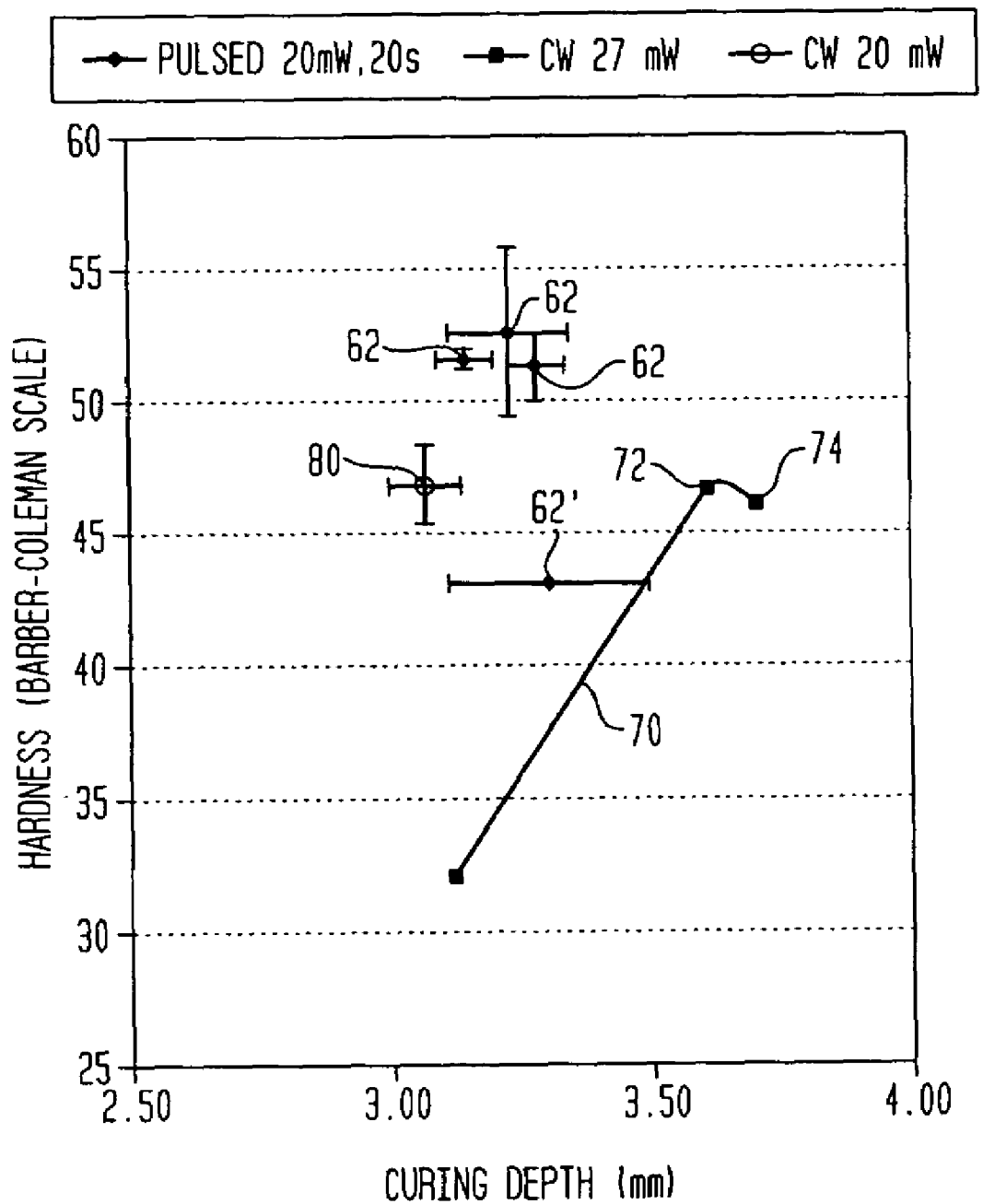
FIG. 6 shows a comparison of surface hardness for samples cured with pulsed light and samples cured using cw light.

Hardness values of samples cured with pulsed light were measured and compared with hardness values measured from samples cured with continuous wave radiation. The hardness values were then plotted relative to cure depth as shown in FIG. 6. The pulsed samples 62, 62' were pulsed for 20 μs at a power level of 20 mW with a pulse duration of 1.5 and 2 μs corresponding with pulse repetition intervals of 3 and 4 μs respectively. One sample cured with continuous light 70 was cured at 27 mW with exposure times of 10, 20, and 30 seconds. Another sample 80 was cured with continuous light at 20 mW for 10 seconds. As can be seen in FIG. 6, it is shown that at a given exposure the resulting depth of cure using a pulsed light 62, 62' is greater than the depth of cure when cured with a continuous wave light 70. It is also surprising to note that the range of hardness values measured for samples cured with pulsed light 62 was higher than the hardness range measured for samples cured with continuous wave light at higher exposures 72, 74. In all but one measurement 62', the hardness of the sample cured with pulsed light 62 was greater for a given exposure than the hardness of the samples cured with continuous wave light 70 at roughly the same cure depth. Applicants have shown herein that decreasing the total exposure of a sample by adjusting the pulse width and pulse repetition intervals results in a more efficient curing method as well as an improvement in the quality of a cured sample.

It is to be understood that specific embodiments of the invention described herein are illustrative of the principles of the invention and that other modifications may be employed which are still within the spirit and scope of the invention. For example, in one alternate exemplary embodiment, the same process may be used to cure photo-curable epoxies used in electronics and opto-electronics packaging and lithography. A specific epoxy may be cured with different parameters, e.g., maximum light intensity or pulse repetition interval, but still the same dynamics of the curing process fall under the present invention.

What is claimed is:

1. A method for curing polymerizable compositions with a pulsed beam of light said method comprising the step of:
   irradiating the polymerizable composition with a beam of pulsed light emitted by at least one Light Emitting Diode (LED) wherein said pulsed light has a pulse duration of between about 0.05 to about 75 μs and a pulse repetition interval of about 0.25 to about 100 μs.

2. The method of claim 1, wherein the cured composition has a higher hardness value than the same composition cured with a continuous wave light source with the same emission spectrum and for the same total exposure.

3. The method in claim 2, wherein the cured composition has a characteristic hardness of about 40 or more on the Barber-Coleman Hardness scale when cured at a power level of 20 mW and a cure duration of 20 seconds.

4. The method in claim 2, wherein the cured composition has a characteristic hardness of about 50 or more on the Barber-Coleman Hardness scale when cured at a power level of 20 mW and a cure duration of 20 seconds.

5. The method of claim 1, wherein said LED irradiates less total exposure than is required for a continuous wave light source with the same emission spectrum to cure a like composition to the same depth of cure.

6. The method of claim 1 wherein said polymerizable composition is a photo-curable dental composition.

7. The method of claim 1, wherein said polymerizable composition comprises liquid acrylic monomers.

8. The method of claim 1, wherein said polymerizable composition comprises camphorquinone as a photoinitiator.

9. The method of claim 1, wherein said polymerizable composition comprises a photoinitiator and wherein said LED emits light that has an excitation peak that falls within about 40 nm of the absorption peak of a said photoinitiator.

10. The method of claim 1, wherein said LED emits blue light.

11. The method of claim 1, wherein, said LED emits light with an excitation peak that falls within the range of 440 to 500 nm on the electromagnetic spectrum.

12. The method of claim 1, wherein said pulse duration is from about 0.1 to about 10 μs.

13. The method of claim 1, wherein said pulse duration is from about 2 to about 3 μs.

14. The method of claim 1, wherein said pulse repetition interval is between about 1 to about 10 μs.

15. The method of claim 1, wherein the pulse repetition interval is from about 2 to about 5 μs.

16. The method of claim 1, wherein said pulse duration and said pulse repetition interval are selected such that the pulse operates with a duty cycle of from about 5 to about 50%.

17. The method according to claim 1, wherein the cured composition has a cure depth of about 2.8 mm or more.

18. The method according to claim 1, wherein the cured composition has a cure depth of about 3 mm or more.

* * * * *